US010309779B2

(12) United States Patent
McArthur

(10) Patent No.: US 10,309,779 B2
(45) Date of Patent: Jun. 4, 2019

(54) SYSTEM AND METHOD FOR MONITORING UNDERWATER ORGANIC SOLID BUILDUP AND RELATED EMISSIONS BACKGROUND

(71) Applicant: Ross McArthur, Chatham, IL (US)

(72) Inventor: Ross McArthur, Chatham, IL (US)

(73) Assignee: Ross McArthur, Springfield, IL (US)

( * ) Notice: Subject to any disclaimer, the term of this patent is extended or adjusted under 35 U.S.C. 154(b) by 0 days.

(21) Appl. No.: 16/031,708

(22) Filed: Jul. 10, 2018

(65) Prior Publication Data

US 2019/0137270 A1    May 9, 2019

Related U.S. Application Data

(60) Provisional application No. 62/582,686, filed on Nov. 7, 2017.

(51) Int. Cl.
| G01C 13/00 | (2006.01) |
| G01N 1/22 | (2006.01) |
| G01N 1/10 | (2006.01) |
| G01N 33/18 | (2006.01) |
| B63B 35/00 | (2006.01) |

(52) U.S. Cl.
CPC ............. *G01C 13/008* (2013.01); *G01N 1/10* (2013.01); *G01N 1/2273* (2013.01); *B63B 2035/008* (2013.01); *B64C 2201/123* (2013.01); *G01N 33/1886* (2013.01); *G01N 2001/1031* (2013.01)

(58) Field of Classification Search
None
See application file for complete search history.

(56) References Cited

U.S. PATENT DOCUMENTS

| 4,621,347 A | 11/1986 | Ostrander |
| 5,075,014 A | 12/1991 | Sullivan |
| 5,201,884 A | 4/1993 | Nicholas |
| 6,520,105 B2 | 2/2003 | Koda et al. |
| 7,554,884 B2 | 6/2009 | Park |
| 7,688,675 B2 | 3/2010 | Chambers et al. |
| 8,060,270 B2 | 11/2011 | Vian et al. |
| 8,154,953 B1 | 4/2012 | Sims et al. |
| 8,193,496 B2 | 6/2012 | Furry |
| 8,825,241 B2 | 9/2014 | Hine |
| 8,880,241 B2 | 11/2014 | Mohamadi |

(Continued)

FOREIGN PATENT DOCUMENTS

| CN | 202481315 U | 10/2012 |
| WO | WO 2012096684 A1 | 7/2012 |
| WO | WO 2015113962 A1 | 8/2015 |

OTHER PUBLICATIONS

Healey et al., "Collaborative Unmanned Vehicles for Maritime Domain Awareness", Proceedings of the 2005 International Workshop on Underwater Robotics, Nov. 9-11, 2005 (Year: 2005).*

(Continued)

*Primary Examiner* — Nathaniel T Woodward

(57) ABSTRACT

The present invention generally relates to monitoring underwater organic solid buildup and related emissions, and more particularly to a monitoring system and method using a sonar-equipped drone watercraft and a monitoring controller in communication with the drone watercraft to monitor the underwater organic solid buildup and related emissions and to analyze and present results of the analysis.

11 Claims, 14 Drawing Sheets

(56) References Cited

U.S. PATENT DOCUMENTS

| | | | |
|---|---|---|---|
| 9,030,203 B2 | 5/2015 | Cho et al. | |
| 9,051,193 B2 | 6/2015 | Fischmann | |
| 9,063,544 B2 | 6/2015 | Vian et al. | |
| 9,091,034 B2 | 7/2015 | Kryzak | |
| 9,096,106 B2 | 8/2015 | Hanson et al. | |
| 2005/0016430 A1 | 1/2005 | Cardoza et al. | |
| 2008/0125920 A1 | 5/2008 | Miles et al. | |
| 2008/0300821 A1* | 12/2008 | Frank | G01V 1/201 |
| | | | 702/150 |
| 2010/0005857 A1 | 1/2010 | Zhang et al. | |
| 2010/0131133 A1 | 5/2010 | Koda et al. | |
| 2014/0256055 A1* | 9/2014 | Pottorf | G01V 9/007 |
| | | | 436/163 |
| 2017/0190421 A1* | 7/2017 | Diez-Garias | A63H 27/12 |
| 2017/0268714 A1* | 9/2017 | Giron | F16L 55/48 |
| 2017/0351258 A1* | 12/2017 | Kim | G05D 1/0094 |
| 2018/0099573 A1* | 4/2018 | Nemoto | B60L 11/1833 |
| 2018/0102854 A1* | 4/2018 | Kimura | H04B 13/02 |
| 2018/0143314 A1* | 5/2018 | Pelletier | G01S 7/295 |
| 2018/0170494 A1* | 6/2018 | Park | B63G 8/001 |

OTHER PUBLICATIONS

R. Prien, "The Future of Chemical In-Situ Sensors", Marine Chemistry 107 (2007) 422-432 (Year: 2007).*

Rossi et al., Gas-Drone: Portable Gas Sensing System on UAVs for Gas Leakage Localization, conference paper, Nov. 2014 (Year: 2014).*

Makar (PW Makar, "Engineered Innovation: The Remotely Operated & Unmanned Acoustic Sonar Sediment Volume and Mapping Survey", LinkedIn SlideShare, Jan. 2016) (Year: 2016).*

* cited by examiner

SYSTEM AND METHOD FOR MONITORING UNDERWATER ORGANIC SOLID BUILDUP AND RELATED EMISSIONS BACKGROUND

RELATED APPLICATIONS

This application claims the benefit of priority of U.S. Provisional Application Ser. No. 62/582,686, filed Nov. 7, 2017, which is herein incorporated by reference to the present application.

FIELD OF THE INVENTION

The present invention generally relates to monitoring underwater organic solid buildup and related emissions, and more particularly to a monitoring system and method using a sonar-equipped drone watercraft and a monitoring controller in communication with the drone watercraft to monitor the underwater organic solid buildup and related emissions and to analyze and present results of the analysis.

BACKGROUND

Water quality monitoring in a body of water, including a lagoon, for example, may include fixed monitoring stations to monitor various water quality parameters such as tidal status, water temperature, salinity, and oxygen contents. These fixed monitoring stations may be designated at various perimeter sites along the body of water and may include sensors that provide continuous monitoring, collecting continuous data at each site.

Though these fixed monitoring stations provide and collect critical water quality information, they generally are limited to collecting data only in accessible areas based primarily on the number of fixed sites. It would therefore be desirable to be able to provide a dynamic water monitoring system having the ability to collect water quality information data in virtually any location, including hard to access and hazardous areas.

BRIEF SUMMARY

According to various embodiments, a lagoon monitoring system comprises a sonar-equipped remote control drone watercraft, a camera-equipped remote control drone aircraft, and a monitoring controller communicatively coupled with the sonar-equipped remote control drone watercraft and the camera-equipped remote control drone aircraft. The monitoring controller can communicate instructions and data to, and can receive data from, the sonar-equipped remote control drone watercraft and the camera-equipped remote control drone aircraft.

The lagoon monitoring system can collect streams of data from various sensors and detectors operating in the watercraft and the aircraft while each navigates in vicinity of a target lagoon under inspection. The various collected streams of data can be time synchronized and analyzed by the monitoring controller. The analyzed data results can be presented at a user interface providing an accurate representation of various parameters of interest associated with the target lagoon under inspection.

It is one advantage of the present invention to provide a system for monitoring underwater organic solid buildup and related emissions background surrounding a body of water, the system including a drone watercraft, a drone aircraft; and a monitoring system controller communicatively coupled to the drone watercraft and the drone aircraft via one or more wireless communication networks, the monitoring system controller is configured to control the drone watercraft and the drone aircraft, and the monitoring system controller is configured to receive and process a first set of data collected by the drone watercraft and a second set of data collected by the drone aircraft.

It is another advantage of the present invention to provide a method of monitoring underwater organic solid buildup and related emissions background surrounding a body of water, the method including transmitting an operational sequence to a monitoring system controller; initializing drones for capturing data samples where the drones may include a drone watercraft and a drone aircraft; updating a multiple sonar watercraft parameters stored on the drone watercraft; collecting sonar data and GPS data from the drone watercraft; updating multiple chemical data collector parameters stored on the drone watercraft; collecting chemical data from the drone watercraft; updating a multiple aircraft parameters stored on the drone aircraft; collecting camera data from the drone aircraft; updating a multiple chemical gas sensor parameters stored on the drone aircraft; collecting chemical gas data from the drone aircraft; analyzing the data samples including a collection of sonar data, GPS data, chemical data, camera data, and chemical gas data, where the plurality of data samples includes a plurality of time information; synchronizing the time information from the data samples to form a synchronized and historical data set; and generating a presentation output from the synchronized and historical data set on a display device, where the presentation output visually represents a topology of the body of water, including a plurality of lagoon structures, a solid mass buildup and a chemical composition of the body of water.

One in implementation, the drone watercraft may include a sonar system, one or more chemical sensors, a GPS system, and a first information processing system having a first computer processor, a first plurality of memory components, a first network interface device, and a first user interface device; the drone aircraft may include a camera viewing system, a gas sensor, and a second information processing system having a second computer processor, a second plurality of memory components, a second network interface device, and a second user interface device; and the monitoring system controller may include a third information processing system having a third computer processor, a third plurality of memory components, a third network interface device, and a third user interface device.

According to various embodiments of the present disclosure, a new and novel method, information processing system, and computer program product, enable the above described lagoon monitoring system.

BRIEF DESCRIPTION OF THE DRAWINGS

The accompanying figures wherein reference numerals refer to identical or functionally similar elements throughout the separate views, and which together with the detailed description below are incorporated in and form part of the specification, serve to further illustrate various embodiments and to explain various principles and advantages all in accordance with the present invention, in which.

DETAILED DESCRIPTION

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated. The terminology used herein is for the purpose of describing particular embodiments only and is not intended to be limiting of the invention.

In order to collect global positioning and depth data from hard to access and hazardous areas a Remote Control (RC) lagoon monitoring system was developed, which can include according to various embodiments a drone watercraft, a drone aircraft, and a monitoring system controller, as will be discussed in more detail below. This system is a platform for the Sonar System to measure lagoon structures and solid mass buildup, plus data collection from both the onboard air and water sensors of chemical make-up of the lagoon under inspection (being monitored).

Figure 1:
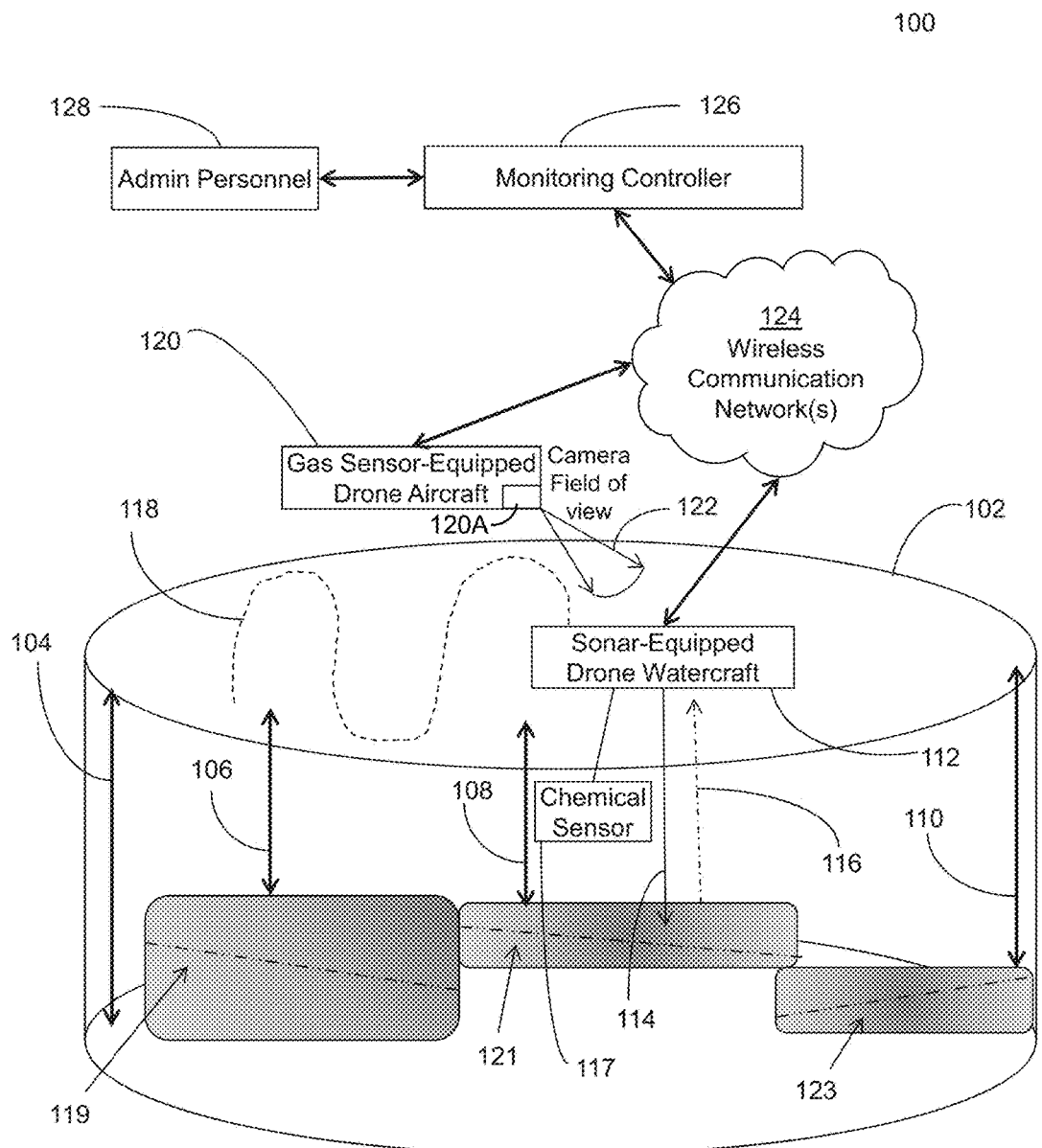
FIG. 1 is a diagram illustrating an example of a lagoon monitoring information processing system, according to an embodiment of the present invention.

Referring to FIG. 1, a lagoon monitoring system 100 is shown. A lagoon 102 is under inspection (being monitored) by one or more of a sonar equipped drone watercraft 112, a gas sensor equipped drone aircraft 120, and a camera viewing system 122 mounted on the drone aircraft 120.

A monitoring system controller 126 is communicatively coupled via one or more wireless communication network(s) 124 with the drone aircraft 120 and the drone watercraft 112. Administrative personnel 128 can operate the monitoring system controller 126 to remotely control the drone watercraft 112 and the drone aircraft 120. In certain embodiments, the drone watercraft 112 and the drone aircraft 120 can operate autonomously by internal programming using software programs, and requiring little or no oversight or remote control by administrative personnel 128.

The drone aircraft 112 follows a flight pattern 118 of traveling over the surface of the water of the lagoon 102. This pattern 118 can be selected to cover with sonar signals the entire topology of the lagoon 102 from end to end.

The sonar signals can be used to measure the varying depths 104, 106, 108, 110, of the lagoon structures 119, 121, 123, which can include liquid and various solid mass layers in the lagoon 102. The sonar signals, according to various embodiments, can be used to measure the depths of layers of solid mass sediment collecting at the bottom of the lagoon 102.

One or more chemical sensors 117 are mounted on board the drone watercraft 112. These chemical sensors 117 can collect chemical data from the lagoon 102 at various depths in the lagoon 102. The chemical sensors 117 can be incrementally lowered into the lagoon 102 from the drone watercraft 112. At each step in lowering the chemical sensors 117 a measurement is taken of the chemical composition of the lagoon 102 at the particular depth.

Optionally, the drone aircraft 120 may include atmospheric gas sensor equipment that can be used to collect measurements of chemical composition of gas emissions from the lagoon 102. The drone aircraft 120 may also include a camera system 120A having a camera field-of-view 122 that can visually monitor the lagoon 102 and the movement and path traveled by the drone watercraft 112 on the surface of the lagoon.

Example Drone Watercraft

Figure 2:
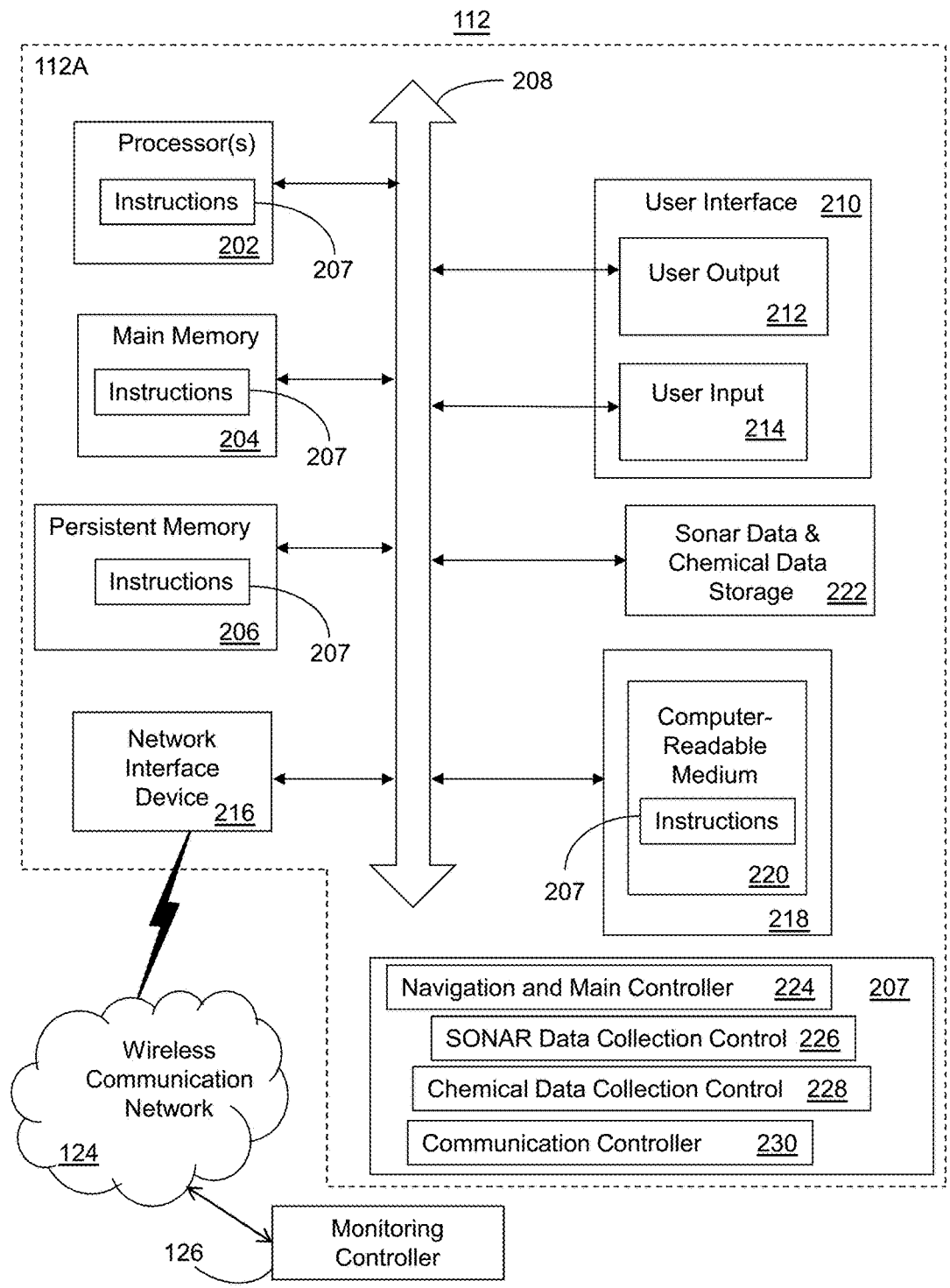
FIG. 2 is a block diagram illustrating a more detailed view of the drone watercraft, in the system illustrated in FIG. 1, according to an embodiment of the present invention.

FIG. 2 illustrates an example of the drone watercraft 112 in the lagoon monitoring system 100 as shown in FIG. 1. This simplified example is not intended to suggest any limitation as to the scope of use or function of various embodiments of the invention described herein. The drone watercraft 112, according to this example, comprises an information processing system 112A which is operational according to various computing system configurations. Examples of well-known computing system configurations that may be suitable for use with the drone watercraft 112 include, but are not limited to, personal computer systems, hand-held or laptop devices, multiprocessor systems, microprocessor-based systems, programmable consumer electronics, network personal computers, and a cloud computing node that includes any of the above systems or devices, and the like.

The information processing system 112A may be described in the general context of computer system-executable instructions, such as program modules, being executed by a computer system. Generally, program modules may include routines, programs, objects, components, logic, data structures, and so on that perform particular tasks or implement particular abstract data types. Information processing system 112A may be practiced in distributed cloud computing environments where tasks are performed by remote processing devices that are linked through a communications network. In a distributed cloud computing environment, program modules may be located in both local and remote computer system storage media including memory storage devices.

Referring to FIG. 2, the information processing system 112A of the drone watercraft 112 is shown in more detail than that shown in the lagoon monitoring system 100 in FIG. 1. The information processing system 112A of the drone watercraft 112 comprises one or more processors 202 communicatively coupled with a main memory 204 and with a persistent memory 206.

The main memory 204 can include computer system readable media in the form of volatile memory, such as random access memory (RAM) and/or cache memory. The information processing system of the drone watercraft 112 may further include other removable/non-removable, volatile/non-volatile computer system storage media. By way of example only, a persistent memory storage system 206 can be provided for reading from and writing to a non-removable, non-volatile magnetic media (not shown and typically called a "hard drive"), or alternatively a flash memory, flash drive, SD Card, USB memory drive, or the like. Although not shown, a magnetic disk drive for reading from and writing to a removable, nonvolatile magnetic disk (e.g., a "floppy disk"), and/or an optical disk drive for reading from or writing to a removable, non-volatile optical disk such as a CD-ROM, DVD-ROM or other optical media can be provided. In such instances, each can be connected to bus 208 by one or more data media interfaces. As will be further depicted and described below, persistent memory 206 may include at least one program product having a set (e.g., at least one) of program modules that are configured to carry out the functions of various embodiments of the invention.

Program/utility, having a set (at least one) of program modules, may be stored in persistent memory 206 by way of example, and not limitation, as well as an operating system, one or more application programs, other program modules, and program data and configuration parameters. Each of the operating system, one or more application programs, other program modules, and program data and configuration parameters, or some combination thereof, may include an implementation of a networking environment. Program modules generally carry out the functions and/or methodologies of various embodiments of the invention as described herein.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

The one or more processors 202 are also communicatively coupled with a reader 218 of computer readable medium 220. The information processing system 112A of the drone watercraft 112 can typically include a variety of computer readable media 220. Such media may be any available media that is accessible by a computer system, and it includes both volatile and nonvolatile media, removable and non-removable media.

A bus architecture 208 facilitates communication between the various system components in the information processing system of the drone watercraft 112. The bus 208 represents one or more of any of several types of bus structures, including any of a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Instructions 207 can be at least partially stored in the computer readable medium 220, the main memory 204, the persistent memory 206, and internal memory cache in the one or more processors 202. Instructions 207 can comprise, for example, computer program software, configuration parameters, and data, used by the one or more processors 202 to execute instructions of the computer program software. The processor 202 executes the instructions, according to various embodiments, and in response to executing the instructions performs features and functions of the information processing system of the drone watercraft 112, as will be discussed in more detail below.

Sonar data & chemical data memory storage 222 is communicatively coupled with the one or more processors 202 and can store at least a portion of sonar data, chemical sensor data, and related data, for processing and communication of the data with other information processing systems such as via the network 124. At least a portion of the sonar data, chemical sensor data, and related data, may be securely stored in an encrypted form that would require a cryptographic key to decrypt and render the stored data usable by an executing information processing system.

The processor 202, according to the present example, is communicatively coupled with a user interface 210. The user interface 210 comprises a user output interface 212 and a user input interface 214. Examples of elements of the user output interface 212 can include a display, a speaker, one or more indicator lights, one or more transducers that generate audible indicators, and a haptic signal generator. Examples of elements of the user input interface 214 can include button switches, slide switches, a keyboard, a keypad, a mouse, a track pad, and a touch pad.

The processor 202, according to the present example, is communicatively coupled with one or more network interface devices 216. The network interface device 216 is communicatively coupled with the wireless communication network(s) 124. The network interface device 216 can communicate with one or more wireless communication network(s) 124 such as a local area network (LAN), a general wide area network (WAN), or a public network (e.g., the Internet), or a combination thereof. The monitoring system controller 126 and the drone aircraft 120 are also communicatively coupled with the wireless communication network(s) 124 as shown. In this way, the drone aircraft 120 can communicate with the monitoring system controller 126 and with the drone aircraft 120 via the network interface device 216.

The instructions 207 include instructions for performing features and functions of the drone watercraft navigation and control by a navigation and main controller 224.

The instructions 207, according to the present example, include instructions for performing features and functions implementing sonar data collection and control 226.

The instructions 207, according to the present example, include instructions for performing features and functions implementing chemical data collection and control 228.

The instructions 207, according to the present example, include instructions for implementing a drone watercraft communications controller 230. The drone watercraft communications controller 230 coordinates communications between the drone watercraft 112 and the network 124.

Example Drone Aircraft

Figure 3:
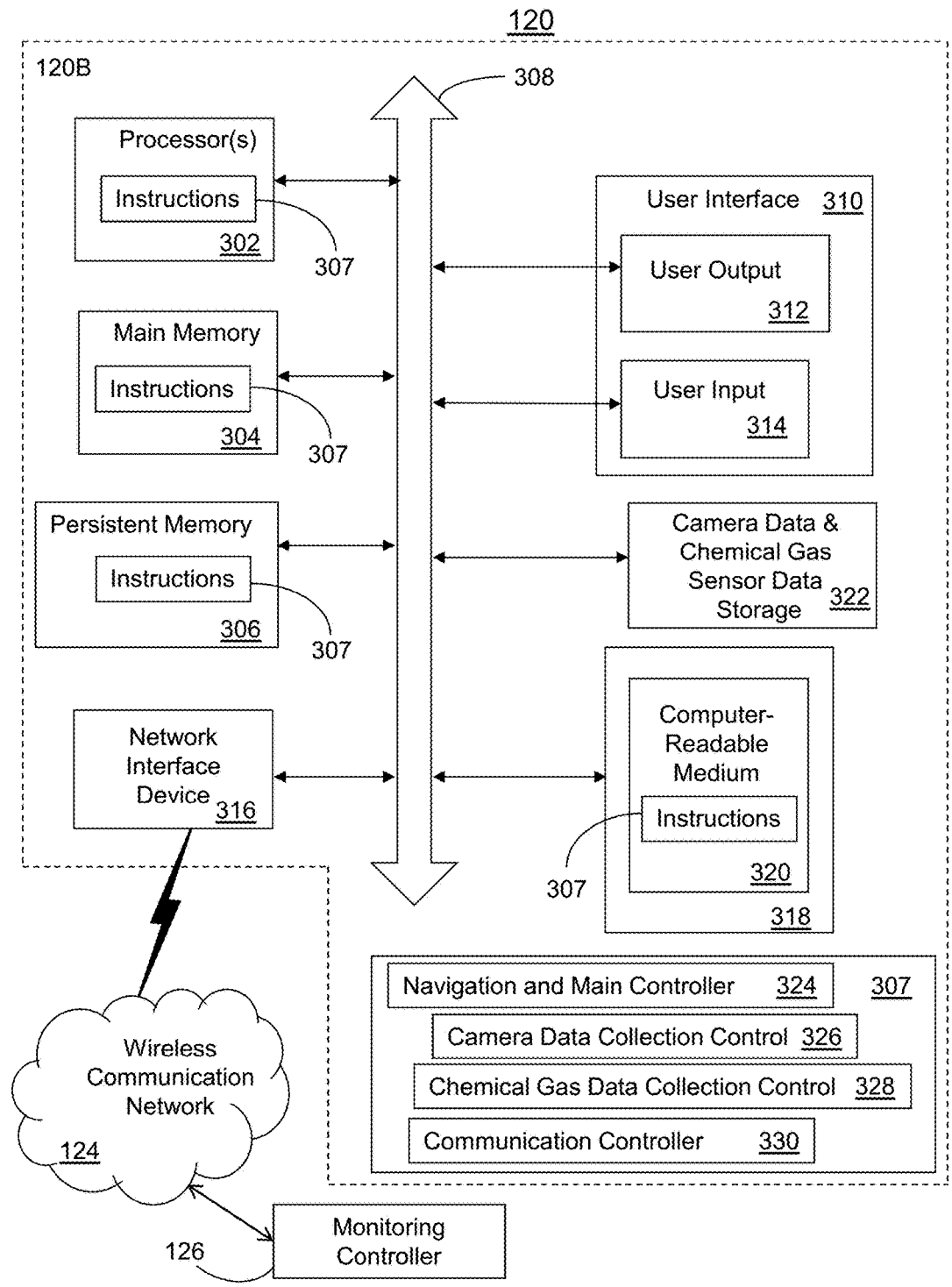
FIG. 3 is a block diagram illustrating a more detailed view of the drone aircraft, in the system illustrated in FIG. 1, according to an embodiment of the present invention.

Referring to FIG. 3, an information processing system 120B of the drone aircraft 120 is shown in more detail than that shown in the lagoon monitoring system 100 in FIG. 1. The information processing system 120B of the drone aircraft 120 comprises one or more processors 302 communicatively coupled with a main memory 304 and with a persistent memory 306.

The main memory 304 can include computer system readable media in the form of volatile memory, such as random access memory (RAM) and/or cache memory. The information processing system 120B of the drone aircraft 120 may further include other removable/non-removable, volatile/non-volatile computer system storage media. By way of example only, a persistent memory storage system 306 can be provided for reading from and writing to a non-removable, non-volatile magnetic media (not shown and typically called a "hard drive"), or alternatively a flash memory, flash drive, SD Card, USB memory drive, or the like. Although not shown, a magnetic disk drive for reading from and writing to a removable, nonvolatile magnetic disk (e.g., a "floppy disk"), and/or an optical disk drive for reading from or writing to a removable, non-volatile optical disk such as a CD-ROM, DVD-ROM or other optical media can be provided. In such instances, each can be connected to bus 308 by one or more data media interfaces. As will be further depicted and described below, persistent memory 306 may include at least one program product having a set (e.g., at least one) of program modules that are configured to carry out the functions of various embodiments of the invention.

Program/utility, having a set (at least one) of program modules, may be stored in persistent memory 306 by way of example, and not limitation, as well as an operating system, one or more application programs, other program modules, and program data and configuration parameters. Each of the operating system, one or more application programs, other program modules, and program data and configuration parameters, or some combination thereof, may include an implementation of a networking environment. Program modules generally carry out the functions and/or methodologies of various embodiments of the invention as described herein.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

The one or more processors 302 are also communicatively coupled with a reader 318 of computer readable medium 320. The information processing system 120B of the drone aircraft 120 can typically include a variety of computer readable media 320. Such media may be any available media that is accessible by a computer system, and it includes both volatile and nonvolatile media, removable and non-removable media.

A bus architecture 308 facilitates communication between the various system components in the information processing system of the drone watercraft. The bus 308 represents one or more of any of several types of bus structures, including any of a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Instructions 307 can be at least partially stored in the computer readable medium 320, the main memory 304, the persistent memory 306, and internal memory cache in the one or more processors 302. Instructions 307 can comprise, for example, computer program software, configuration parameters, and data, used by the one or more processors 302 to execute instructions of the computer program software. The processor 302 executes the instructions, according to various embodiments, and in response to executing the instructions performs features and functions of the information processing system 120B of the drone aircraft 120, as will be discussed in more detail below.

Camera data & chemical gas sensor data memory storage 322 is communicatively coupled with the one or more processors 302 and can store at least a portion of camera data, chemical gas sensor data, and related data, for processing and communication of the data with other information processing systems such as via the network 124. At least a portion of the camera data, chemical gas sensor data, and related data, may be securely stored in an encrypted form that would require a cryptographic key to decrypt and render the stored data usable by an executing information processing system.

The processor 302, according to the present example, is communicatively coupled with a user interface 310. The user interface 310 comprises a user output interface 312 and a user input interface 314. Examples of elements of the user output interface 312 can include a display, a speaker, one or more indicator lights, one or more transducers that generate audible indicators, and a haptic signal generator. Examples of elements of the user input interface 314 can include button switches, slide switches, a keyboard, a keypad, a mouse, a track pad, and a touch pad.

The processor 302, according to the present example, is communicatively coupled with one or more network interface devices 316. The network interface device 316 is communicatively coupled with the network 124. The network interface device 316 can communicate with one or more networks such as a local area network (LAN), a general wide area network (WAN), or a public network (e.g., the Internet), or a combination thereof. The monitoring system controller 126 and the drone watercraft 112 are also communicatively coupled with the network 124 as shown. In this way, the drone aircraft 120 can communicate with the monitoring system controller 126 and with the drone watercraft 112 via the network interface device 316.

The instructions 307 include instructions for performing features and functions of the drone aircraft navigation and control by a drone aircraft navigation and main controller 324.

The instructions 307, according to the present example, include instructions for performing features and functions implementing camera data collection and control 326.

The instructions 307, according to the present example, include instructions for performing features and functions implementing chemical gas sensor data collection and control 328.

The instructions 307, according to the present example, include instructions for implementing a drone aircraft communications controller 330. The drone aircraft communications controller 330 coordinates communications between the drone aircraft 120 and the wireless communication network(s) 124.

It should be noted that the drone aircraft 120 can be used as a message signal relay communication system between the drone watercraft 112 and the monitoring system controller 126. This would allow the message signals transmitted by either one of the drone watercraft 112 and the monitoring system controller 126 to be received by the other one utilizing the drone aircraft 120 to provide a wireless communication path. This would make it easier to remotely control and communicate with the drone watercraft 112 from the monitoring system controller 126 even if there is no direct line of communication transmission between the drone watercraft 112 by the monitoring system controller 126. It can also significantly extend the distance from the monitoring system controller 126 that the drone watercraft 112 can be operated and remotely controlled in a particular lagoon 102.

Example Monitoring System Controller

Figure 4:
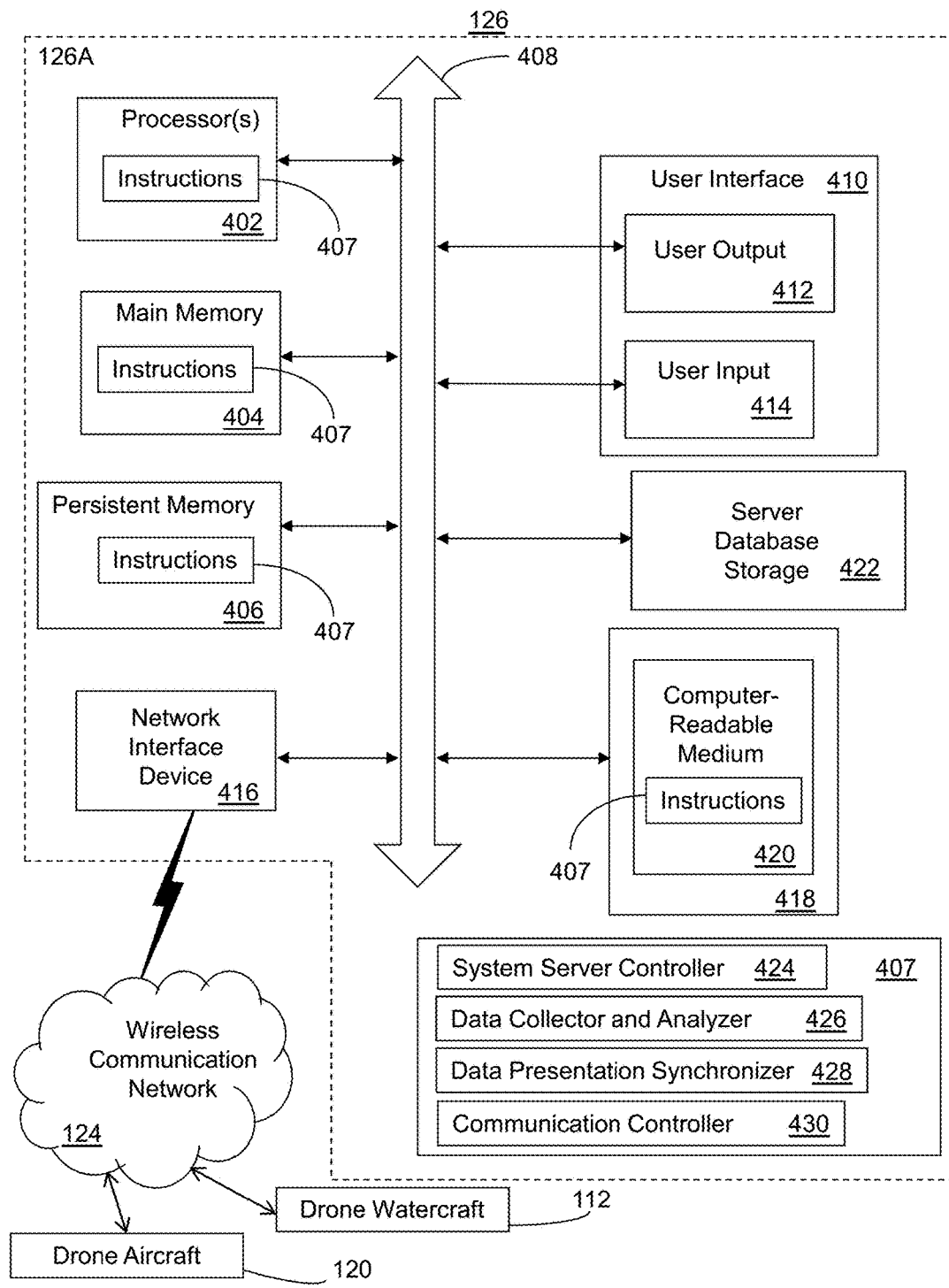
FIG. 4 is a block diagram illustrating a more detailed view of the monitoring controller, in the system illustrated in FIG. 1, according to an embodiment of the present invention.

Referring to FIG. 4, an information processing system 126A of the monitoring system controller 126 is shown in more detail than that shown in the lagoon monitoring system 100 in FIG. 1. The information processing system 126A of the monitoring system controller 126 comprises one or more processors 402 communicatively coupled with a main memory 404 and with a persistent memory 406.

The main memory 404 can include computer system readable media in the form of volatile memory, such as random access memory (RAM) and/or cache memory. The information processing system of the monitoring system controller 126 may further include other removable/non-removable, volatile/non-volatile computer system storage media. By way of example only, a persistent memory storage system 406 can be provided for reading from and writing to a non-removable, non-volatile magnetic media (not shown and typically called a "hard drive"), or alternatively a flash memory, flash drive, SD Card, USB memory drive, or the like. Although not shown, a magnetic disk drive for reading from and writing to a removable, nonvolatile magnetic disk (e.g., a "floppy disk"), and/or an optical disk drive for reading from or writing to a removable, non-volatile optical disk such as a CD-ROM, DVD-ROM or other optical media can be provided. In such instances, each can be connected to bus 408 by one or more data media interfaces. As will be further depicted and described below, persistent memory 406 may include at least one program product having a set (e.g., at least one) of program modules that are configured to carry out the functions of various embodiments of the invention.

Program/utility, having a set (at least one) of program modules, may be stored in persistent memory 406 by way of example, and not limitation, as well as an operating system, one or more application programs, other program modules, and program data and configuration parameters. Each of the operating system, one or more application programs, other program modules, and program data and configuration parameters, or some combination thereof, may include an implementation of a networking environment. Program modules generally carry out the functions and/or methodologies of various embodiments of the invention as described herein.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

The one or more processors 402 are also communicatively coupled with a reader 418 of computer readable medium 420. The information processing system of the monitoring system controller 126 can typically include a variety of computer readable media 420. Such media may be any available media that is accessible by a computer system, and it includes both volatile and non-volatile media, removable and non-removable media.

A bus architecture 408 facilitates communication between the various system components in the information processing system of the drone watercraft. The bus 408 represents one or more of any of several types of bus structures, including any of a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Instructions 407 can be at least partially stored in the computer readable medium 420, the main memory 404, the persistent memory 406, and internal memory cache in the one or more processors 402. Instructions 407 can comprise, for example, computer program software, configuration parameters, and data, used by the one or more processors 402 to execute instructions of the computer program software. The processor 402 executes the instructions, according to various embodiments, and in response to executing the instructions performs features and functions of the information processing system 126A of the monitoring system controller 126, as will be discussed in more detail below.

Server database storage 422 is communicatively coupled with the one or more processors 402 and can store at least a portion of sonar data, chemical data, camera data, chemical gas sensor data, and related data, for processing and communication of the data with other information processing systems such as via the network 124. At least a portion of the sonar data, chemical data, camera data, chemical gas sensor data, and related data, may be securely stored in an encrypted form that would require a cryptographic key to decrypt and render the stored data usable by an executing information processing system 126A.

The processor 402, according to the present example, is communicatively coupled with a user interface 410. The user interface 410 comprises a user output interface 412 and a user input interface 414. Examples of elements of the user output interface 412 can include a display, a speaker, one or more indicator lights, one or more transducers that generate audible indicators, and a haptic signal generator. Examples of elements of the user input interface 414 can include button switches, slide switches, a keyboard, a keypad, a mouse, a track pad, and a touch pad.

The processor 402, according to the present example, is communicatively coupled with one or more network interface devices 416. The network interface device 416 is communicatively coupled with the wireless communication network(s) 124. The network interface device 416 can communicate with one or more networks such as a local area network (LAN), a general wide area network (WAN), or a public network (e.g., the Internet), or a combination thereof. The drone aircraft 120 and the drone watercraft 112 are also communicatively coupled with the wireless communication network(s) 124 as shown. In this way, the monitoring system controller 126 can communicate with the drone aircraft 120 and the drone watercraft 112 via the network interface device 416.

The instructions 407 include instructions for performing features and functions of a monitoring system server controller 424.

The instructions 407, according to the present example, include instructions for performing features and functions implementing data collection and analysis 426.

The instructions 407, according to the present example, include instructions for performing features and functions implementing a data presentation synchronizer 428. The various collected data, received from the drone aircraft 120 and the drone watercraft 112 via the network interface device 416, are processed and synchronized in time with each other, for analyzing and presenting the analyzed data results, such as via the user interface 410.

The instructions 407, according to the present example, include instructions for implementing a monitoring system communications controller 430. The communications controller 430 coordinates communications between the monitoring system controller 126 and the wireless communication network(s) 124. Overview of Monitoring System Components Watercraft Construction:

In one implementation, the drone watercraft 112 may be configured as having a 39" (1)×12" (h)×15" (w) fiberglass "Displacement" hull, ⅛th think, with a single 8 volt brushless motor with direct drive.

Watercraft Control:

For manual operations, the drone watercraft 112 may be controlled by a technician (administrative personnel) using a single remote controller (e.g., 2.4 Hz Tactic RC Transmitter/Receiver with a wireless range of up to 1500 feet).

Watercraft Automated System:

The drone watercraft 112 may also be controlled by the automated navigation steering system. For example, by using a Digikey 497-15069-2-ND Accelerometer with a Raspberry Multiplex it is possible to download a latitude and longitude pattern to run a precise course. This ability is to measure the exact data of a waterway year after year.

Example Watercraft Tablet Control System:

By the use of any commercial tablet (or other controller) it is possible to synchronize the automated navigation steering system (i.e., Digikey 497-15069-2-ND Accelerometer with a Rasberry Multiplexer) with a 2.4 Hz antenna to allow for remote control of the drone watercraft 112 with the tablet. The software on the tablet allows for manual control and predetermined patterns of the boats course. This system is based on its ability to access a wireless network.

Sonar System:

According to one example in a sonar system, a transducer, including for example an Airmar P39 Smart Transducer with a depth range of 700', may be mounted in the bottom of the hull of the drone watercraft 112 pointing directly down. The transducer sends an NMEA 183 signal to a Actisense Multiplexer to marry the signal from a Digikey DT-800 GPS with a data recovery board, including a memory storage device or SD Card reader.

In some implementations, single beam, multi-beam, and side beam sonar scanners for data collection on the drone watercraft 112 may be used.

Software:

By inserting a memory device, including a Secure Digital (SD) memory card, from the drone watercraft 112 into a monitoring system controller/computer, a customized software program may automatically project the depth, latitude and longitude into a three dimensional color image showing the contours of the lagoon bottom. The image can be manipulated, turned, rotated with the use of the user's mouse. The software includes an algorithm that can calculate the total solid and liquid matter of the area that has been scanned.

Example Drone Aircraft System:

By placing the camera 122 on the drone aircraft 120 (e.g., 3DR Solo quadcopter) it is possible to capture video and synchronize the patterns created by the drone watercraft 112 from previous patterns.

The gas sensor may be mounted on the drone aircraft 120 and can detect and measure water conductivity, ORD and HP levels, plus measure the ammonia, methane and carbon-sulfates gases in the air directly over the water's surface for baseline readings. The gas sensor may include, for example, a MultiRae Gas Sensor and a Hanna HI 9829 Multimeter. By flying the drone aircraft 120 in a spiral motion over the target lagoon under inspection (being monitored), the drone aircraft 120 can tail-off in a downwind direction to detect and measure the gas composition and gauge the dissipation of these chemical emissions.

Next, the several sets of data may be married (synchronized) to provide a clear picture of the organic buildup in the lagoon, the water quality and the emissions given off by the facility.

Example Monitoring System Operation

Figure 5:
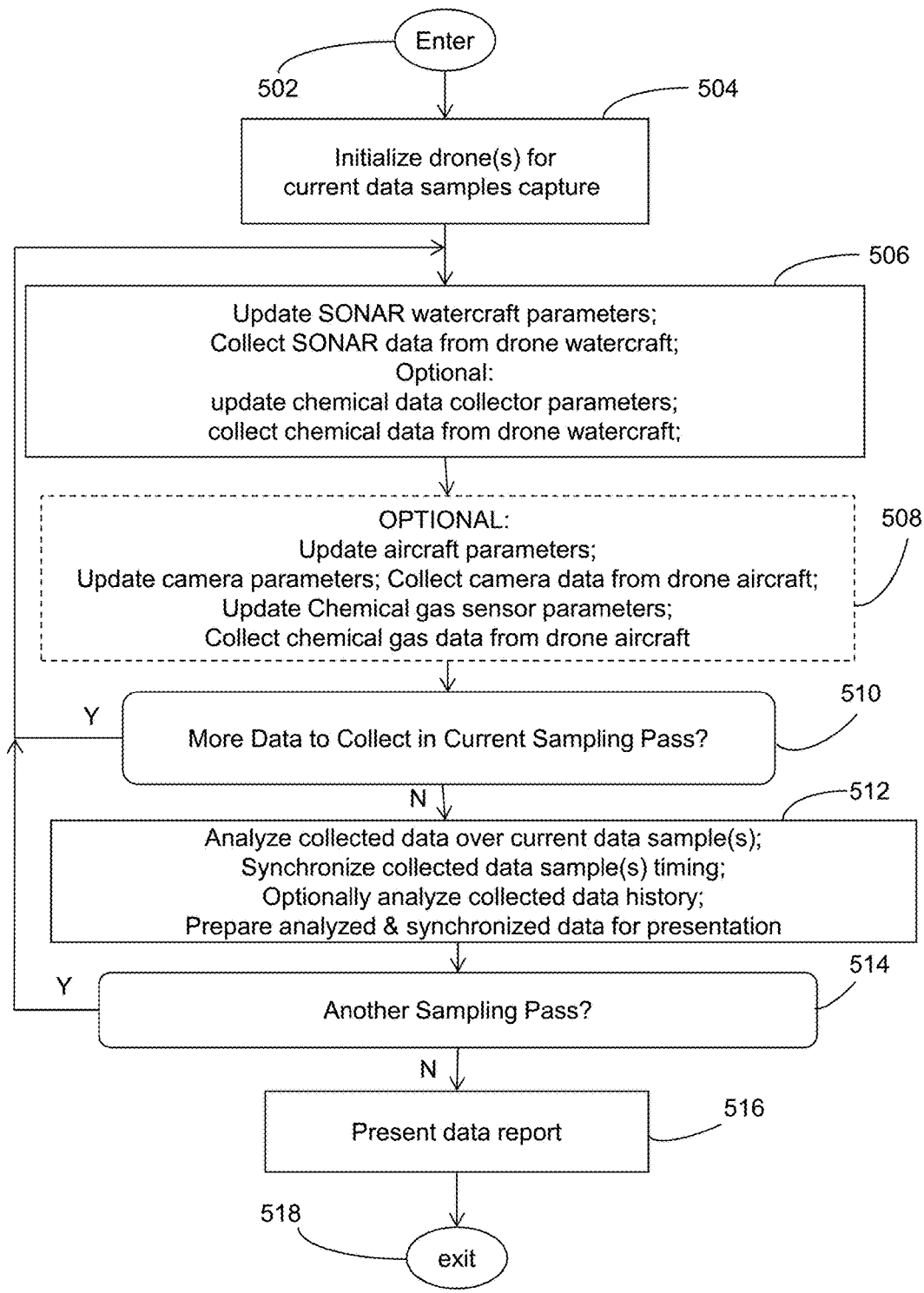
FIG. 5 is a flow diagram illustrating an example operational sequence performed with the monitoring controller shown in FIG. 4, the drone aircraft shown in FIG. 3, and the drone watercraft shown in FIG. 2, according to an embodiment of the present invention.

Referring to FIG. 5, the operational sequence is entered, at step 502, and the monitoring system controller 126 initializes one or more drones for capturing current data samples, at step 504. The monitoring system controller 126, at step 506, updates the sonar watercraft parameters and collects sonar data from the drone watercraft 112. In certain embodiments, that include chemical sensors communicatively coupled with the drone watercraft 112, the monitoring system controller 126 updates chemical data collector parameters and collects chemical data from the drone watercraft 112.

Optionally, according to various embodiments including the drone aircraft 120, the monitoring system controller 126 updates, at step 508, aircraft parameters which can include camera parameters and chemical gas sensor parameters.

The monitoring system controller 126 determines, at step 510, whether there is more data to collect in the current sampling pass. If there is more data to collect, at step 510, then the process returns to step 506 to collect more sonar data, optionally collect chemical data, camera data, and chemical gas sensor data.

When there is no more data to collect, at step 510, the monitoring system controller 126 analyzes, at step 512, the collected data over the current data samples. Additionally, the collected data samples are synchronized with each other over time. Optionally, the monitoring system controller 126 analyzes the collected data over the current data samples and also uses in the analysis collected data history from previous collected data samples. The monitoring system controller 126 prepares the analyzed and synchronized data from the various sources, for presentation to administrative personnel 128, such as via the user interface 410.

The monitoring system controller 126 determines, at step 514, whether to perform another data sampling pass. If another data sampling pass is to be performed, at step 514, then the process returns to step 506. If another data sampling pass is not performed, at step 514, the monitoring system controller 126 presents the data, at step 516, such as via the user interface 410, to administrative personnel 128. The presentation of the data, at step 516, can report the data using various types of presentation tools. For example, the information can be presented using charts, graphs, two dimensional images, three dimensional images, augmented reality images, virtual reality images, audio, text, and graphics. The operational sequence is then exited, at step 518. Examples of presentation tools via the user interface will be discussed below.

Figure 6:
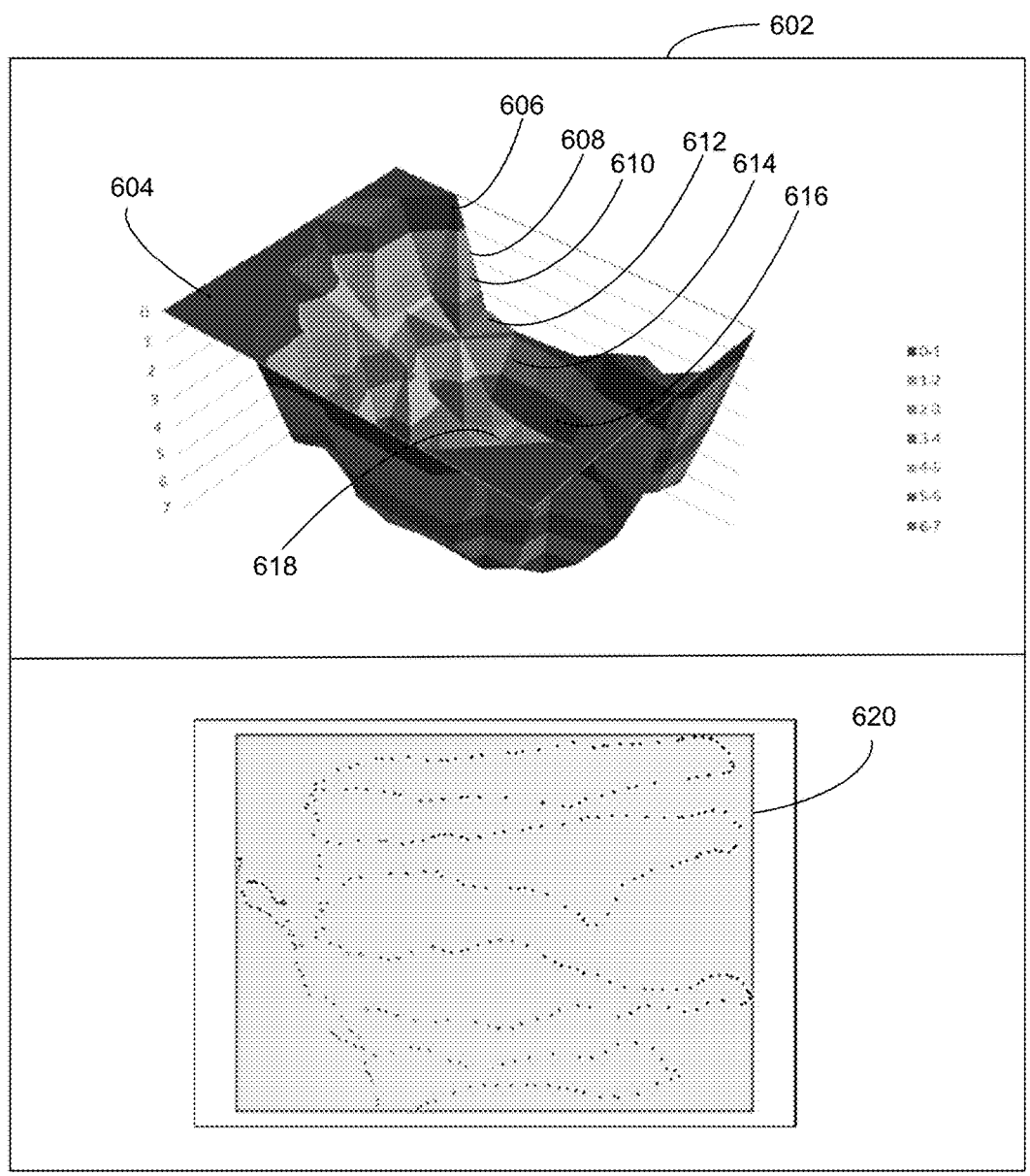
FIG. 6 depicts a first example user interface suitable for displaying information related to the system of FIG. 1, according to an embodiment of the present invention.

FIG. 6 illustrates a three dimensional image 602 showing several levels of depth in a target lagoon under examination. Additionally, a map 620 of sonar sample coordinates is shown identifying the various locations of the drone watercraft moving over the surface of the lagoon.

FIG. 6 includes a first user interface 602 showing multiple levels 604, 606, 608, 610, 612, 614, 616, 618, of depth measured using sonar equipment on board the drone watercraft illustrating a topology of the lagoon. FIG. 6 also includes a second user interface 620 showing a map of the various locations where the watercraft took data samples from the lagoon.

From depth level 604 all the way down to depth level 618 illustrate different depths in triangulation and color indicating the various depths. Also, to the left in the image is a scale, numbered zero to seven which is a quick reference to depth, as well.

A legend shown on the right of the image gives a reference of the various depth levels of the lagoon as measure using sonar sensor(s) onboard the drone watercraft. In the presentation, color is used to show a scale of the various depths. This provides quick reference to the user by showing different color scales on depth and then, as can be seen, various undulations of the bottom of the lagoon, which reflect in this image depth and contour of the lagoon. In addition to lagoons, other water bodies may include lakes, a ponds or any other shallow bodies of water.

Those depth measurements were made using the sonar signal from the sonar equipment on the drone watercraft 112. In the current example, there are two sonar scanners. A first one is aimed for measuring a down scan. The down scan sends a signal from the transducer in the drone watercraft 112, which is just basically a ping. It sends five of these pings every second. The ping goes down until it hits a structure or a solid point and then bounces back to the aperture in the transducer. The time taken between the ping and the reception of that signal is an indication of depth and a GPS device onboard the watercraft provides global location coordinate data giving the exact position globally of that depth at that ping.

The triangulation process measures a smooth contour of the lagoon at various depths. A triangulation measurement takes the latitude, longitude, and depth, which is a triangle, so that's called triangulation.

The second user interface 620, shows a map of all the data points. Each one of those points on the map indicates location of the drone watercraft 112, the sonar transducer and sensor being aimed straight down into the lagoon, and measuring a depth.

It is taking a ping (sonar beam) to the bottom, at that GPS point of the trip. The left side of the image indicates where the drone watercraft entered the lagoon and started taking measurements. The drone watercraft 112 then traveled in generally a grid-type pattern across the surface of the lagoon, moving back and forth while measuring depth with sonar at specific data points.

The sonar beam goes from top surface of the lagoon to bottom in a cone shape. So for example when the sonar equipment sends out a sonar signal, if it's a half-inch diameter signal at the surface, and some of these measured depths are seven, eight, and ten feet, the signal forms into a cone shape. So it gives a broad stroke of the depth in those areas. While the second user interface 620 appears to map a single point, when looking at lagoon depth contour 610 or 612 in the first user interface 602 the signal cone diameter is much greater diameter at the measured depth. For example, it can be probably 12 inches on either side of that point shown in the second user interface 620. That is 24 inches in diameter at that particular GPS point and depth measurement.

The measurements are taken in an overlapping pattern traveled by the drone watercraft 112 which results in very accurate data. It is showing true bottom.

At the measurements along the edges of the lagoon, where ping signal is hitting the edge of the lagoon, there's shown some build-up or sediment. The lagoon 102 is typically angulated. It has an angle of 3 to 1 or 4 to 1 from the edge of the lagoon travelling inward into the lagoon as seen in the first user interface 602. The angle of the slope goes down to true bottom. That is for example every three feet out into the lagoon, it goes down one foot.

This lagoon 102 does have solid matter in it. So level 618 shows a level of organic matter on the bottom surface of the lagoon 102.

Level 618 is showing approximately seven feet of solid matter in this example.

It should be noted that the first user interface and the second user interface in FIG. 6 illustrate a profile of the lagoon 102 at specific areas of the lagoon 102. It has the ability to isolate a specific area of a lagoon/waterway and then separate it from the rest of the image allowing us to view the lagoon object to calculate the mass, then spin and rotate the image to view from different angles. It provides the ability to identify the lagoon as a set of building blocks, where a user can utilize the monitoring system controller 126 to analyze and tear down an image (whether it be liquid or solid) and then build it back up. It allows the technician/administrative personnel 128 to collect accurate data on volume and mass of structures of the lagoon 102.

Figure 7:
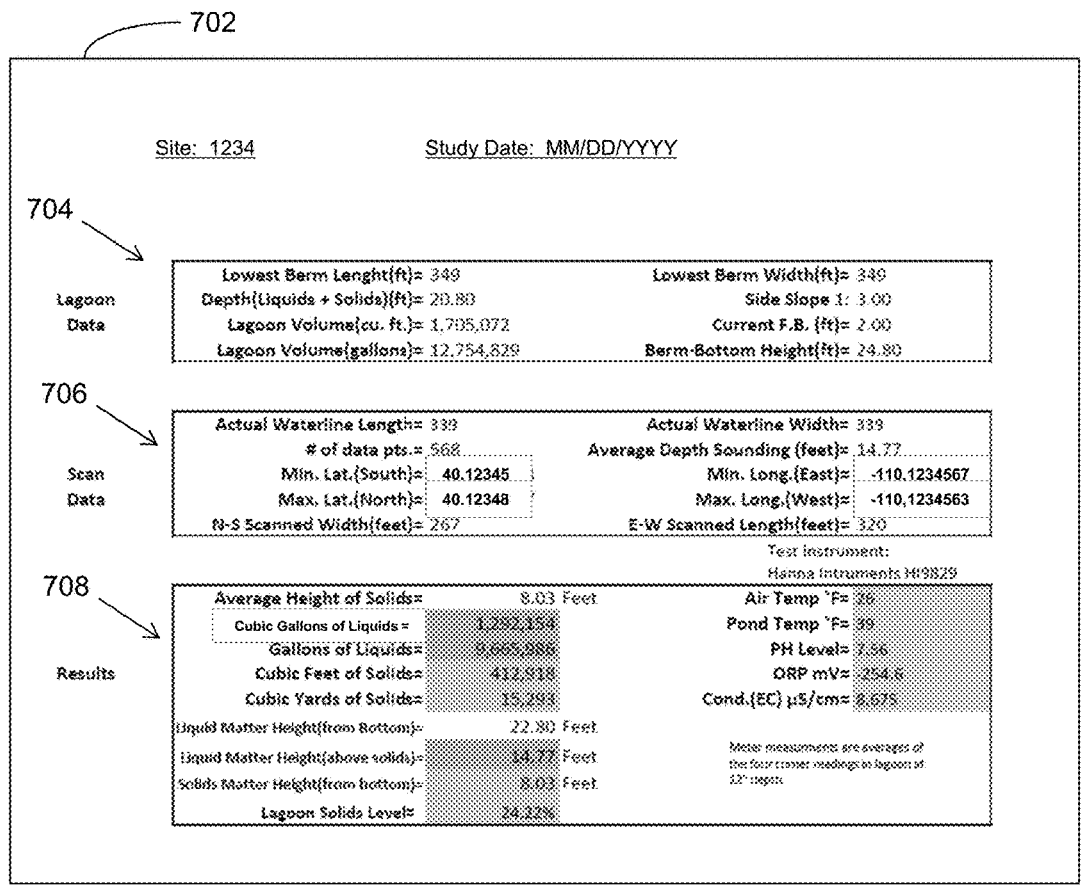
FIG. 7 depicts a second example user interface suitable for displaying information related to the system of FIG. 1, according to an embodiment of the present invention.
Figure 8:
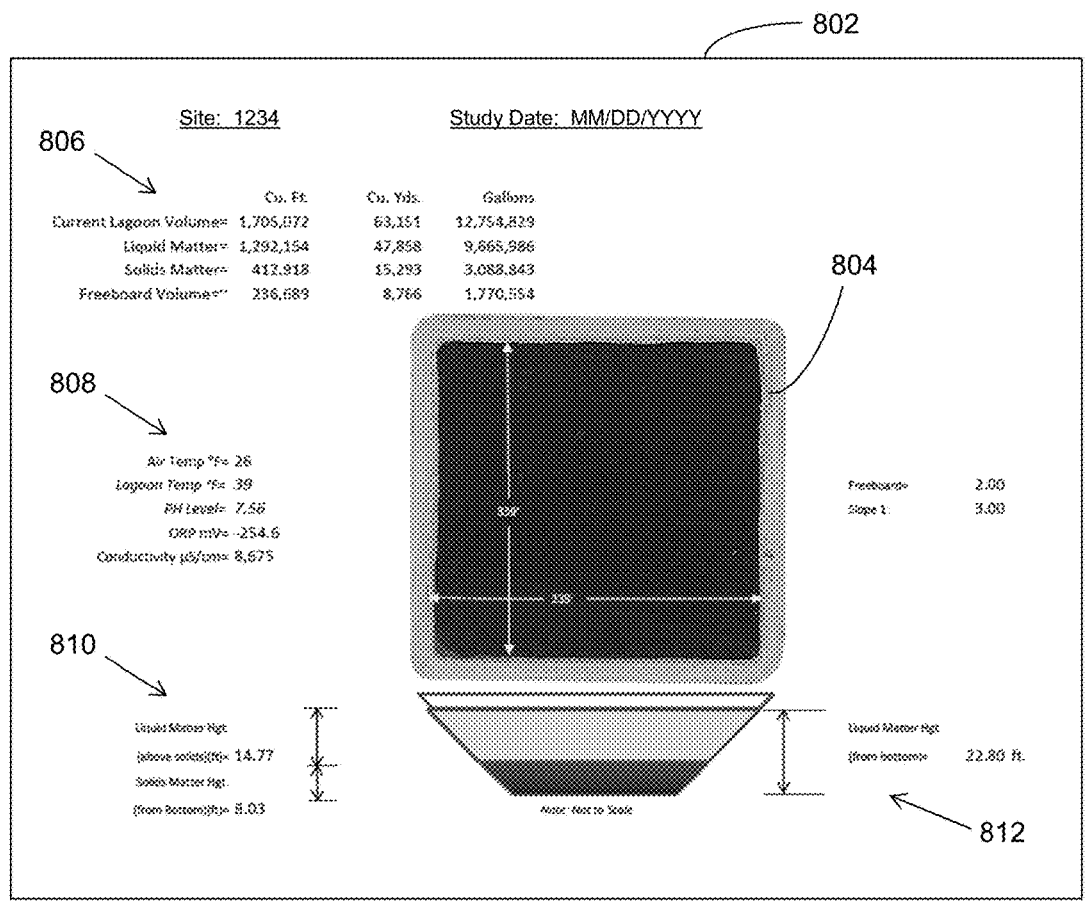
FIG. 8 depicts a third example user interface suitable for displaying information related to the system of FIG. 1, according to an embodiment of the present invention.

As shown also in the examples of FIG. 7 and FIG. 8, the data charts and image elements 812 and 810 show various lagoon measurements and sensor readings. This additional information in FIG. 7 and FIG. 8 complement the images in FIG. 6 to provide an accurate picture of the lagoon topology, including showing any solid mass buildup and chemical composition.

The image elements 812 and 810 illustrate a side-layer view of the lagoon 102. That image of the lagoon 102 can be rotated in the analysis by the monitoring system controller 126.

With reference to the example of FIG. 7, the user interface portion at 704 shows the actual physical measurements of the berm according to the present example. The electronic measuring equipment onboard the drone watercraft 112 measures the actual physical size of the out-to-out of the lagoon, or the buildout of the lagoon. In this example, it is looking for total lagoon capacity, not only below the surface but what is above the surface. What is the lowest point on the berm in case there was a flood? How much liquid can the basin contain before it floods out of there? So the monitoring system controller 126 can analyze the collected sonar data and GPS data and determine the lowest berm length. It then combines that with the depth and the liquid number with the sonar signals. Then, the monitoring system controller 126 can calculate an approximation of the cubic feet and gallons of the lagoon and the various depth measurements. So cubic feet would be solid and gallons would be liquid, and on the right side of that is shown the length, 349 ft., the slope at a 3:1 angle, the current freeboard, FB stands for freeboard, from the surface to the lowest point of that berm. So the berm bottom height indicates the total combination from the bottom of this lagoon to the lowest point of the berm is 24.8 feet high. That is not the water level. That would be 22.8 ft. The lowest point of the lagoon basin would be 24.8 feet. Now that's where it starts to flood, if any more water is added to the lagoon. For example, it got to 24.9 feet, it would be flooding out of that lagoon basin. The user interface portion indicated by figure element 706 shows information about the actual waterline length. In this calculation, according to the example, it does not include the berm like it does in FIG. 6. The second point is the number of data points that were taken. That is the lagoon from earlier. It shows the minimum latitude and maximum longitude. It shows the global positioning of the lagoon. Then it shows the distance of the scan, so if the lagoon itself is 339 feet long in water surface, the widest scan done by the drone watercraft was 267 feet long to approximately 30 feet from the shore on either side. Average depth down was 14.77, so that made the average depth approximately 8 feet. Then it shows the minimum latitude and longitude measurements. The user interface portion indicated by figure element 708 shows information about the results calculated from the scans shown in the user interface portion indicated by figure element 706. All of this data is very useful for monitoring the health of the lagoon and the development of the buildup of sediment and solid mass material at the bottom of the lagoon basin.

Descriptions of Non-Limiting Example Operations of the Lagoon Monitoring System

A lagoon can be a basin that has sloped sides and a flat bottom typically located toward the center of the lagoon. For example, a lagoon can have sides that are sloped down at a slope angle of one foot down toward the bottom of the lagoon for every three feet out to the middle of the lagoon, until the sloped sides reach the flat bottom of the basin. So, if in the example the depth of the basin is twenty feet at the center flat bottom, the sides of the basin can angle out from the outer edge of the lagoon by sixty feet to reach the twenty foot bottom of the basin. The construction of the lagoon basin is known. The depth of the bottom of the lagoon basin and the angle of each of the sloped sides are known.

For example, if the true bottom of the lagoon basin is a rectangle of sixty feet by sixty feet, then the overall size of the lagoon at the surface is approximately 180 feet by 180 feet. The formed by the lagoon basin true bottom and true side surfaces can be defined with a known mathematical formula.

As another simplified example, the volume of a cylindrical basin would be defined by the following mathematical formula, i.e., Volume=Pi times (radius of the cylinder) squared times the height of the cylindrical basin. Again, the volume formed by the lagoon basin true bottom and true side surfaces can be defined with a known mathematical formula.

An overall volume of a basin of a lagoon can be determined by mathematical calculations based on known dimensions and geometry of the basin. Sediment and solid mass material are deposited in the lagoon basin and accumulate over time into a volume of solid mass material at the bottom of the lagoon under water.

At a desired time for inspection of the lagoon, the remote control sonar equipped water craft can be deployed to travel on the surface of the water in the lagoon following a determined pattern, or grid, and at determined GPS coordinates covering with downward aimed active sonar signals the current bottom surfaces of the lagoon basin. By emitting downward aimed active sonar pulse signals and measuring the time duration to detecting a return sonar echo signal, the sonar system equipped watercraft can measure a depth (a range) from the surface of the lagoon to the current bottom of the lagoon at determined GPS coordinates. The depth measurement is calculated by multiplying the speed of sound in water (e.g., averaging 1,500 meters per second) by the time between emission and echo return. These measurements can be taken at thousands of points on the surface of the lagoon. At each point the sonar system on the watercraft determines the current GPS coordinate and the current depth of the water from the surface of the water to the current bottom, which includes any sediment and solid mass accumulated on top of the true bottom of the lagoon basin.

Each point is identified by a latitude coordinate determined from a GPS signal, a longitude coordinate determined from a GPS signal, and a depth coordinate determined with the active sonar aimed downward into the lagoon basin. A collection of these points, and at each point compared with the known depth of the true bottom and side surfaces of the lagoon basin, can be analyzed to determine a volume of water on top of the sediment and solid mass material that is built up on top of the known depth of the true bottom and side surfaces of the lagoon basin. Additionally, the analysis can determine the volume of sediment and solid mass material that is under water and built up on top of the known depth of the true bottom and side surfaces of the lagoon basin.

In certain embodiments, the collection of points can be used to create an image of a flowing top surface of the volume of sediment and solid mass material that is under water and built up on top of the known depth of the true bottom and side surfaces of the lagoon basin. By imaging the surface of the sediment and solid mass material at the bottom of the lagoon basin the overall health of the lagoon and the rate of growth of the layer, or layers, of sediment and solid mass material that is under water and built up on top of the true bottom and sides of the lagoon basin.

In some embodiments the calculation of how much liquid is in the lagoon basin and how much solid mass material (e.g., organic solid mass material) can be a very valuable measurement of the health and maintenance record of the lagoon. It can be used by waste management personnel and government agencies to monitor the growth of the waste (e.g., animal waste product) accumulating at the bottom of the lagoon basin. Based on one or more measurements of the current depth (or optionally the estimated average depth) of the sediment and organic solid mass material layer that is being built-up in the lagoon basin over time, it can indicate how much time remains before the growing buildup of sediment and organic solid material will become a hazardous condition for humans, animals, and/or the environment. Before such a hazardous condition is reached, the management of such a facility including the lagoon can take remedial actions to reduce the sediment and organic solid material buildup on the bottom of the lagoon. For example, and not for limitation, the management can order a waste removal service to suction out the underwater sediment and organic solid material layer until it is reduced back to acceptable levels for managing operations of the facility. This will vary from facility to facility. However, the above process of repeated measurements can be customized for various different types of operations and requirements to maintain a safe and healthy lagoon based facility.

As another example, the buildup of the underwater sediment and organic solid material layer can be repeatedly measured and monitored over time such that the level of the volume of water on top of the sediment and organic solid material layer is maintained to acceptable operational levels to avoid an anticipated amount of water rushing into the lagoon and causing a hazardous lagoon overflow condition. The amount of water rushing into the lagoon can be predicted such that its volume added in combination with the existing volume of the water already in the lagoon will not exceed a certain height of a berm or other landmark associated with the lagoon basin to avoid hazardous overflow conditions.

Further, the remote control watercraft can include a chemical sensor system that can measure chemical composition of the water in the lagoon at or near the top surface of the water. Such chemical sensor measurements can include water PH, ORP, conductivity, or other chemical composition parameters that may be desired to be monitored according to the requirements a particular facility. Additionally, the chemical sensor system may include a tether and a remotely controllable wench system that can selectively lower the chemical sensor into the water at one or more desired depths, such as at six feet, ten feet, or another depth level. At each point (i.e., defined by latitude, longitude, and depth of the water) in the lagoon additionally one or more chemical composition measurements can be taken of the lagoon water. The collection of these measurements can additionally indicate the current health of the lagoon.

Additionally, in certain embodiments, a drone aircraft can measure the chemical gas emissions of the lagoon into the ambient air surrounding the lagoon. The gas emissions can be sensed at varying heights above the surface of the water in the lagoon. The collection of these measurements can additionally indicate the current health of the lagoon. It can also indicate potential noxious gas emissions or other hazardous condition of the lagoon facility.

Example of a Method for Collecting Sonar Data from a Lagoon

The sonar equipped remote control watercraft 112 includes sonar transducer(s) that are aimed down from the surface of the water toward the bottom of the lagoon. This type of sonar active signaling is also referred to as Sonar "Down Scan".

[The "Down Scan" sonar measures the depth of the water at a given point on the surface of the water in the lagoon. This point can be defined by a plurality of data entries, including location coordinates from a GPS receiver which can be part of the equipment on the remote control watercraft 112. The location coordinates can include GPS latitude and GPS longitude of the drone watercraft 112. The point can additionally be defined by a depth measurement of the water to the bottom of the lagoon basin as measured by one or more sonar readings at the given point. This data point can be collected as a record in a database along with many other data points (records in the database) covering many different locations on the lagoon according to a determined pattern, e.g., a grid pattern, traversed by the moving watercraft on top of the surface of the water in the lagoon. Each data entry for a data point (for a record) corresponds to a field in the record of the particular data point on the lagoon. This collection of data points (collection of records in the database) can include other related information (e.g., other related information fields stored in each record) regarding the lagoon. For example, at a given data point the watercraft can measure with chemical sensor(s) a chemical composition of the water in the lagoon at the surface of the water. This measurement could be added to a field in the record of the particular data point. In certain embodiments, the chemical sensor(s) can be selectively lowered by the watercraft 112 to one or more determined depths. These one or more measurements could be added to one or more corresponding fields in the record of the particular data point.

Additionally, in certain embodiments, a drone aircraft 120 can measure the chemical gas emissions of the lagoon into the ambient air surrounding the lagoon. The chemical gas emissions can be sensed at varying heights above the surface of the water in the lagoon. Each of these measurements could be added to a field in a record in the database, each data point corresponding to a drone aircraft location given by GPS coordinates indicated by GPS latitude and GPS longitude of the remote control drone aircraft 120. Additionally, a height above the water level of the water in the lagoon basin can be added as another field in a record in the database. Additionally, each measurement of a chemical being sensed by the drone aircraft 120 can be stored in another field in a record in the database. The collection of these data points (collection of these records in the database) can additionally indicate the current health of the lagoon. It can also indicate potential noxious gas emissions or other hazardous conditions of the lagoon facility.

With location coordinates and sonar depth readings from thousands of collected data points in a database that can be stored in the monitoring controller 126, or in another information processing system communicatively coupled with the monitoring controller 126, the monitoring controller 126 can accurately determine an average depth over the entire body of water in the lagoon basin. This average depth reading over the collection of data points provides an accurate estimate of how much water volume is in the lagoon basin and how much sediment and solid mass material is at the bottom of the lagoon. It should be noted that the true depth of the lagoon basin is known at all data points in the collection of data points. Each data point corresponds to a known true bottom of the lagoon basin from known information provided by the construction of the lagoon, such as from an operator of a lagoon-equipped facility. An accurate estimate of the volume of sediment and solid mass material buildup on the true bottom of the lagoon can be calculated using mathematical calculations based on the sonar measured depth for each data point in the collection of data points and compared with the known depth of the true bottom of the lagoon basin at each data point.

Lastly, a time information field can be added to each record in the database. This time information corresponds to when the particular measurement was taken which is also a field in the particular record in the database. By including time information with each record stored in the database, a history of the developing volume of sediment and solid mass material buildup on the true bottom of the lagoon, the developing chemical composition of the lagoon water at one or more depths, and the developing chemical composition of the ambient atmospheric air at one or more heights above the surface of the water, can be maintained and monitored for a facility.

Non-Limiting Example Calculations:

1—You multiply the length times width time the build-out depth times 2.14 (that is the slope angel) to equal the total volume.

2—You multiply the length times width times the average depth given you by the sonar to equal the liquid volume.

3—You minus the Liquid Volume from the Total Volume to arrive at Solid Volume.

For example: 1—100×100×20=200,000 cubic feet Total Volume

[2—100×100×10=100,000 cubic feet Liquid Volume, the cubic feet may be converted to liquid gallons by multiplying 7.4.

3—200,000−100,000=100,000 cubic feet Solid Volume.

The monitor system controller 126 can generate a 3D image of the surfaces of the sediment and solid mass material buildup layer on the true bottom of the lagoon by utilizing a 3D imaging program and using the sonar depth readings and the corresponding known true bottom depth data for every data point in the lagoon basin.

The sonar system can create a series of "Triangulation" (latitude, longitude and depth) data points, which can be entered into an Excel worksheet. These data points in the Excel worksheet can form an image that can be displayed on a user interface, such as a user interface of an information processing system associated with the monitoring controller 126. Additionally, using the Microsoft Excel program the image can be moved and rotated and turned, such as by scrolling the mouse back and forth. These three dimensional (3D) views into the surfaces of the sediment and solid mass material buildup layer on the true bottom of the lagoon can provide additional valuable information indicating the overall condition of the sediment and solid mass material buildup layer and the health of the lagoon.

Additionally, the collection of data points in a database and the 3D Excel Microsoft Image can be presented to administrative personnel of a facility such as on one or more separate pages of a display.

Figure 9:
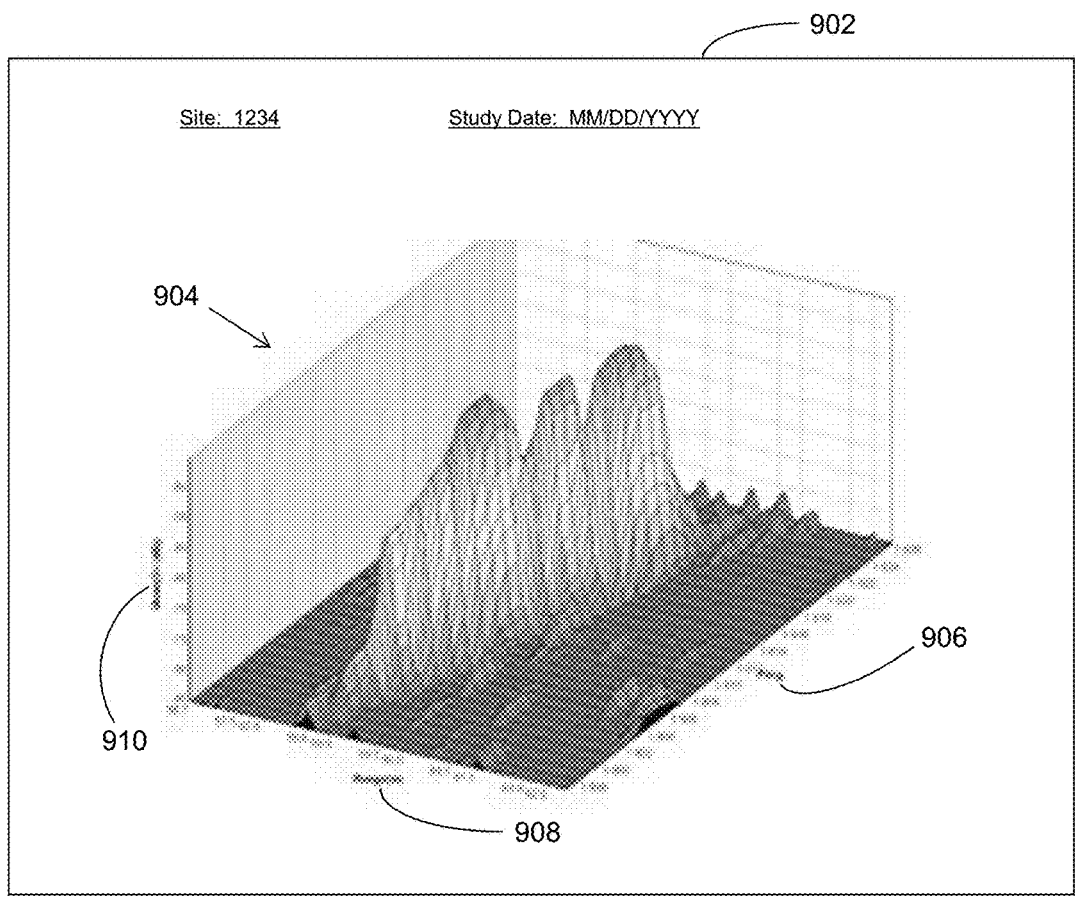
FIG. 9 depicts a fourth example user interface suitable for displaying information related to the system of FIG. 1, according to an embodiment of the present invention.
Figure 10:
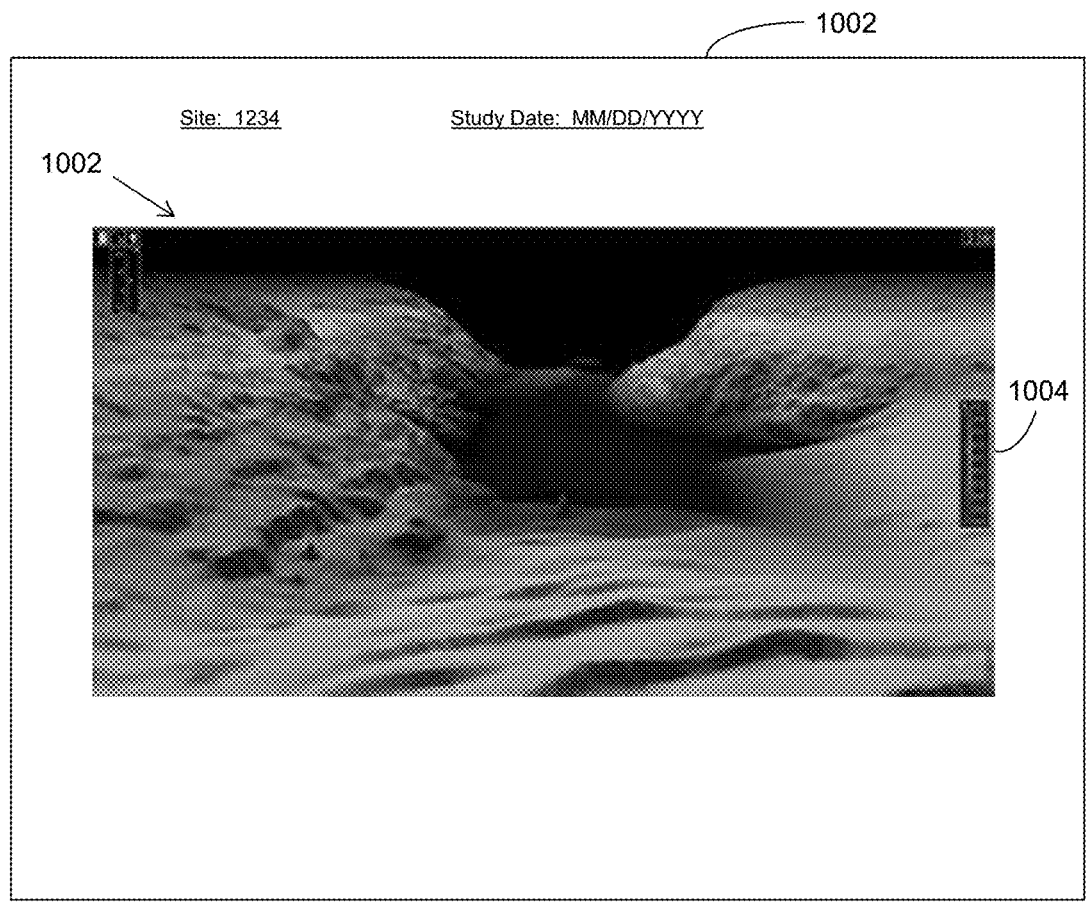
FIG. 10 depicts a fifth example user interface suitable for displaying information related to the system of FIG. 1, according to an embodiment of the present invention.

The images shown in FIG. 9 and FIG. 10 are from a "Side Scan" sonar that show similar imaging information to that from the "down scan" sonar can be additionally collected using "Side scan" sonar. FIG. 9 shows a display 902 of a graph view 904 of data points collected from side scan sonar. The coordinates 906, 908, 910, of the data points are also indicated in the graph view 904. FIG. 10 shows a display 1002 of an image view 1002 of a portion of a lagoon. The image view 1002 includes a legend 1004 to indicate various data conditions shown in various levels of color in the image 1002, which are not readily visible in the gray scale image shown in FIG. 10.

Sonar Wand

Figure 11:
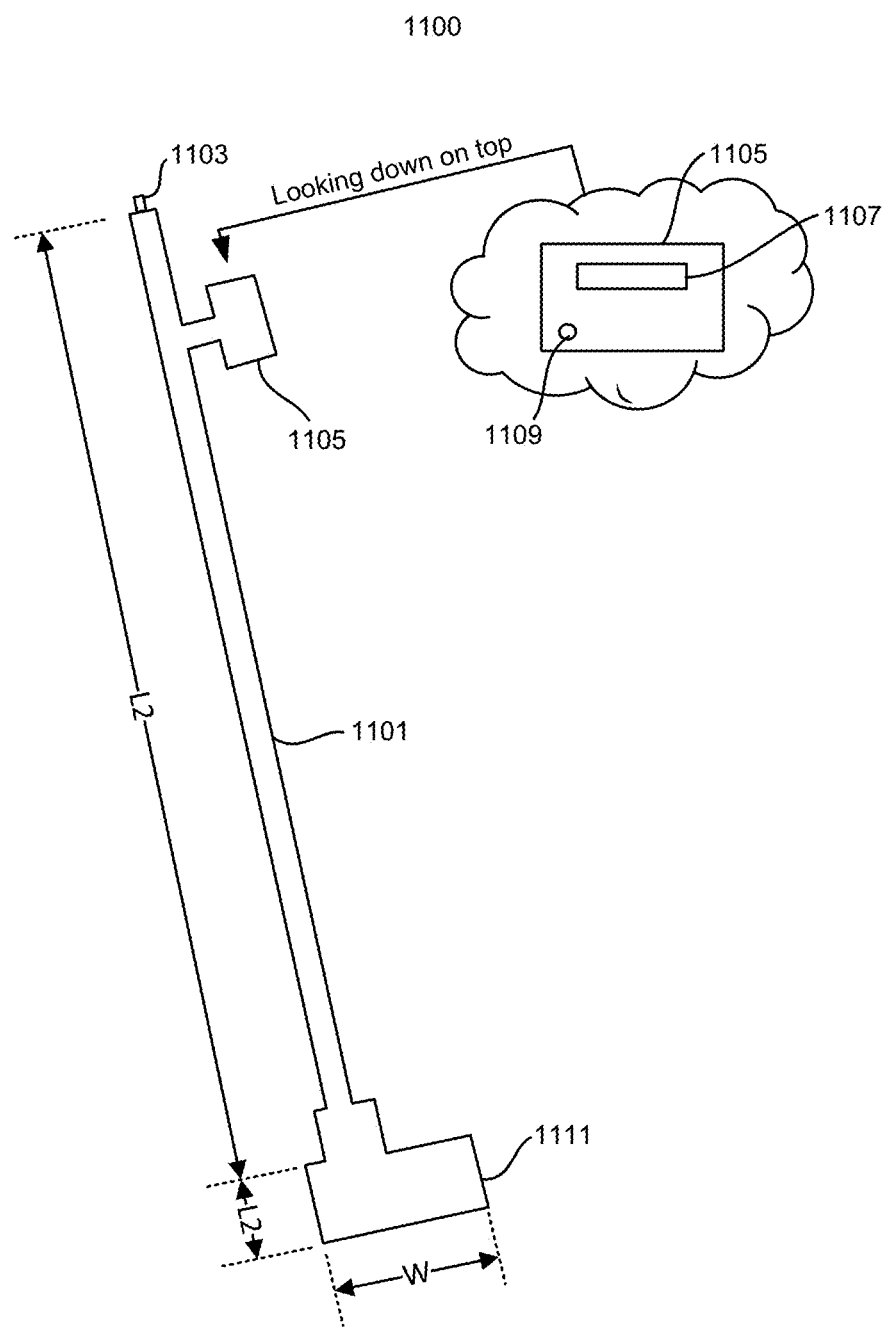
FIG. 11 illustrates a sonar wand, according to an embodiment of the present invention.

FIG. 11 illustrates a drawing of a sonar wand 1100 according to another embodiment. The sonar wand 1100 may include a tube body 1101, an activation switch 1103 coupled to one end of the tube body 1101, a computer housing 1105 coupled to a top portion of the tube body 1101, the computer housing 1105 having an LED Display 1107 for displaying and indicating depth and a power switch 1109, and a transducer housing 1111 coupled to the bottom portion of the tube body 1101, the transducer housing 1111 including at least a sonar transducer (not shown). In one implementation, the tube body 1101 may be configured to have a length L1 of 4', the approximate transducer housing length may be configured to have a length L2 of approximately 4" and a width W of approximately 6". In practice, the sonar wand 1100 may provide accurate depth measurements through substrate e.g.: lagoon covers, wood, ice etc.

In operation, a user may press a button on the sonar wand 1100 to send a single pulse created by a microcontroller board such as an Arduino board to a microprocessor to boast a high frequency signal through a substrate then receive the signal back in milliseconds to calculate a time into linear feet thus measuring a distance through water, sewage, liquid, etc.

Components:
6500 Hz transducer
6 volt battery
Housing
Arduino Board
Micro Processor
Pulse limiter
LED display board
Assorted wiring, on/off switch Purpose:

By getting the average depth, measuring the length and width of the area, you can calculate the liquid and organic volume of a lagoon.

Figure 12:
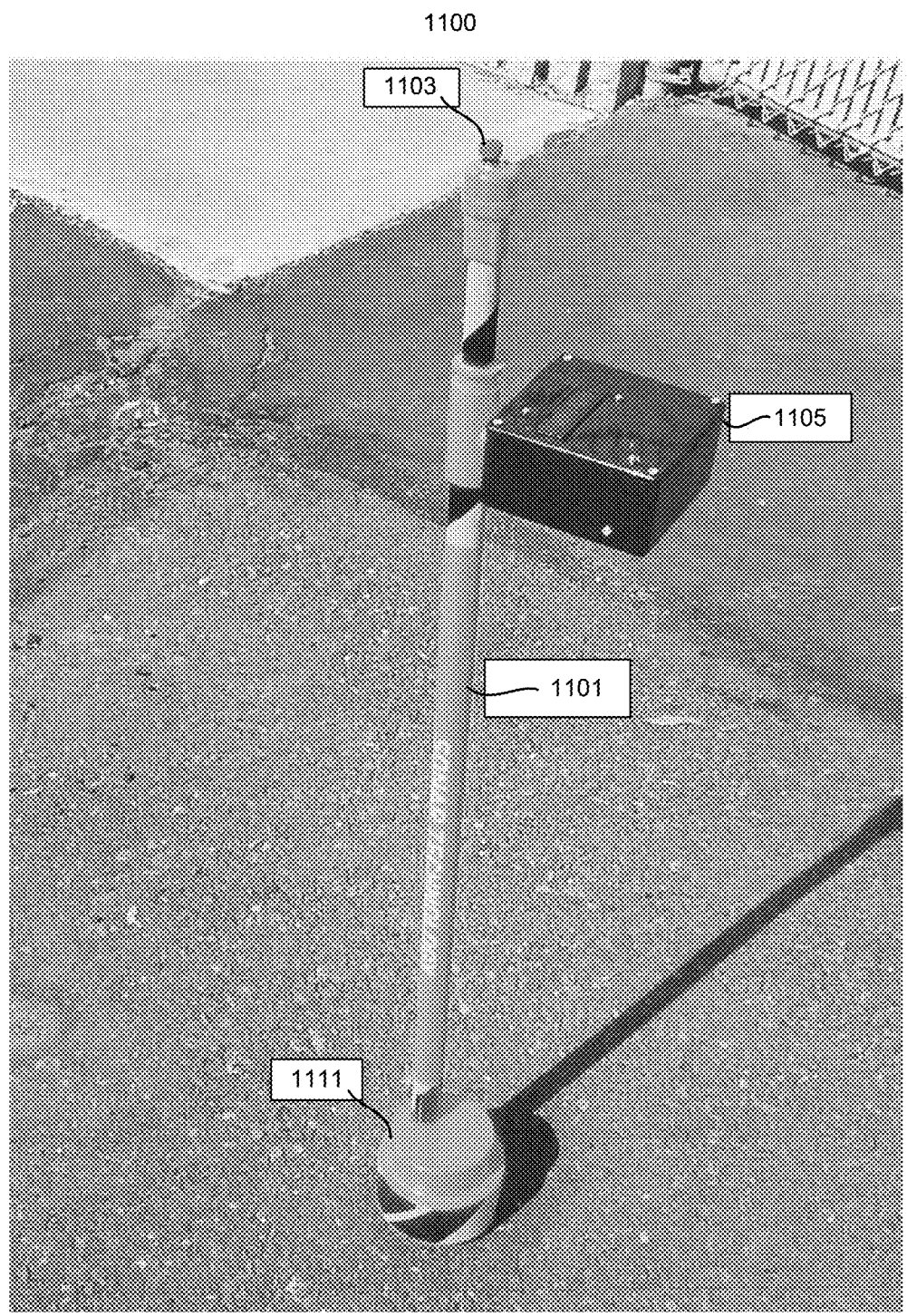
FIG. 12 illustrates a photograph the sonar wand.

FIG. 12 illustrates a photograph the sonar wand 1100, including the tube body 1101, the activation switch 1103 the computer housing 1105 and the transducer housing 1111.

Figure 13:
FIG. 13 illustrates an aerial view taken by a drone aircraft of multiple lagoon systems.

FIG. 13 illustrates an aerial view taken by a drone aircraft of multiple lagoon systems.

Figure 14:
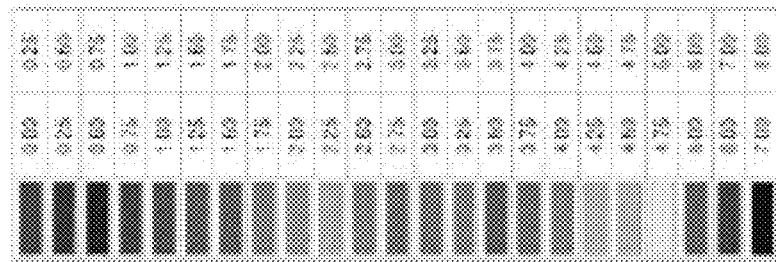
FIG. 14 illustrates a heat map of a lagoon system.
Figure 14:
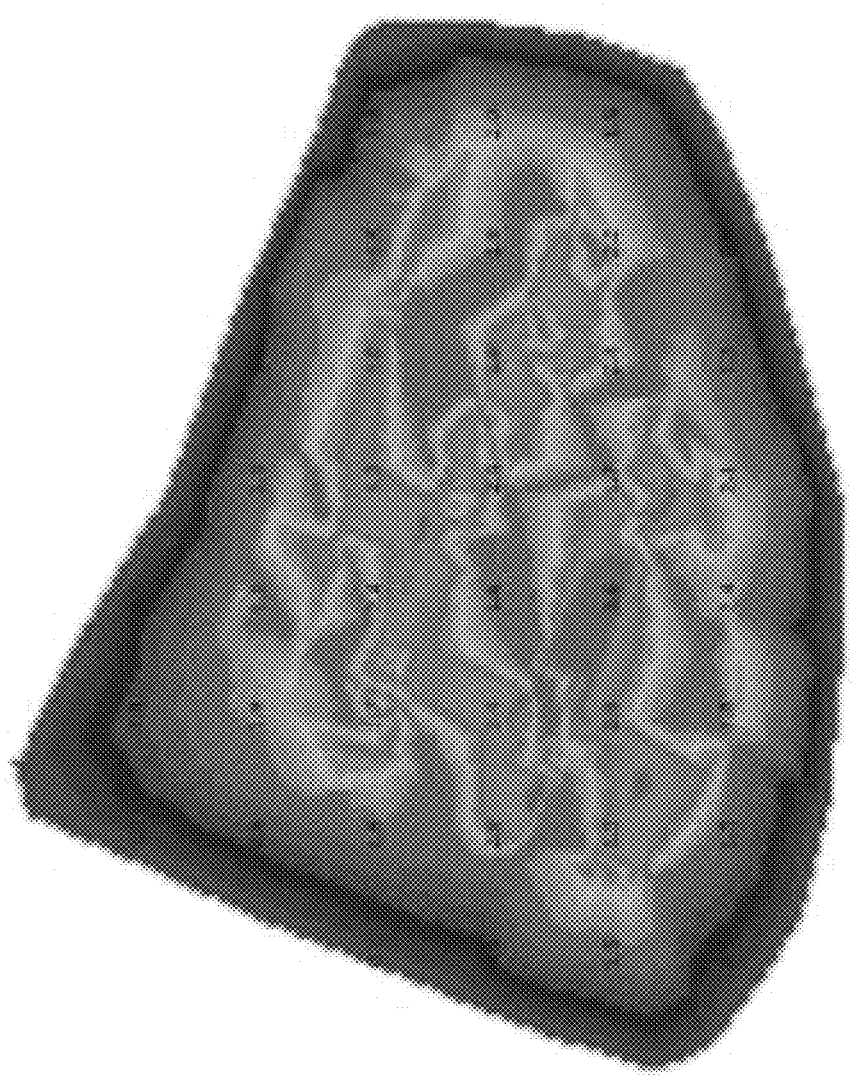

FIG. 14 illustrates a heat map of a lagoon, including a polishing lagoon of a 2 cell 25 old year facultative wastewater lagoon system for a small town in the U.S. Design depth and depth at the time of survey 5' deep. Measurements shown on the profile depict the amount of water above the measured top of the sludge in the lagoon.

What is claimed is:

1. A method of monitoring and calculating a plurality of lagoon-related data for maintaining a lagoon with known dimensions and geometry constructed in a lagoon facility wherein the plurality of lagoon-related data includes a volume of a sediment and solid mass material buildup deposited or formed at a bottom portion of the lagoon and a volume of a body of water on top of the sediment and solid mass material buildup, the method comprising the steps of:

transmitting an operational sequence to a monitoring system controller, wherein the monitoring system controller includes at least a microprocessor and a database;

initializing a drone watercraft for capturing a plurality of data samples over a time period, wherein the drone watercraft is equipped with one or more sonar transducers configured as a down scan sonar or a side scan sonar, a GPS device, and a network interface device, wherein the plurality of data samples include a plurality of sonar data and GPS data, and wherein the monitoring system controller is communicatively coupled via one or more wireless communication networks with the drone watercraft;

updating a plurality of sonar watercraft parameters stored on the drone watercraft;

storing the plurality of sonar data and GPS data in the database;

determining an average sonar depth reading over an entire portion of the lagoon from the plurality of sonar data and GPS data in the database, wherein the volume of the sediment and solid mass material buildup and the volume of the body of water on top of the sediment and solid mass material buildup is determined using the average sonar depth reading and the known dimensions and geometry of the lagoon.

2. The method of claim 1, further comprising: synchronizing a plurality of time information from the plurality of data samples over the time period to form a synchronized and historical data set and generating a presentation output from the synchronized and historical data set on a display device, wherein the presentation output visually represents a topology of the lagoon, including a plurality of structures surrounding the lagoon and the sediment and solid mass material buildup, wherein the presentation output includes charts, graphs, two dimensional images, three dimensional images, augmented reality images, virtual reality images, audio, text, graphics, or a combination thereof.

3. The method of claim 1, further comprising:
analyzing the plurality of sonar data and the GPS data via the monitoring system controller to determine a berm length; and
calculating an approximation of a volume of the lagoon and a plurality of depth measurements via the monitoring system controller.

4. The method of claim 1, wherein the lagoon includes a basin having a plurality of sloped sides and a flat bottom.

5. The method of claim 4, wherein the plurality of sloped sides and the flat bottom of the basin determine a geometry and a total volume of the basin.

6. The method of claim 1, wherein the volume of the sediment and solid mass material buildup and the volume of the body of water on top of the sediment and solid mass material buildup is generated by a 3D imaging program using the average sonar depth reading over the entire portion of the lagoon.

7. The method of claim 1, wherein the down scan sonar or a side scan sonar is configured for measuring various depths of the lagoon at a given data point.

8. The method of claim 7, wherein the given data point is defined by a plurality of data entries, including a plurality of location coordinates from the GPS device.

9. The method of claim 8, wherein the given data point is defined by a depth measurement as measured by one or more sonar readings at the given data point.

10. The method of claim 8, wherein the given data point is collected as a record in the database along with a plurality of other data points covering many different locations of the lagoon according to a predetermined pattern, including a grid pattern, traversed by the drone watercraft traveling on a top surface of the body of water in the lagoon.

11. The method of claim 1, wherein the volume of a sediment and solid mass material buildup deposited or formed at the bottom portion of the lagoon provides an indication of growth of waste matter accumulating on the basin of the lagoon.

* * * * *